United States Patent
Sporbert et al.

(10) Patent No.: US 7,458,812 B2
(45) Date of Patent: *Dec. 2, 2008

(54) THREE-DIMENSIONAL OCCLUSAL AND INTERPROXIMAL CONTACT DETECTION AND DISPLAY USING VIRTUAL TOOTH MODELS

(75) Inventors: Peer Sporbert, Berlin (DE); Hans Imgrund, Berlin (DE); Dimitij Kouzian, Berlin (DE); Stephan Maetzel, Berlin (DE); Rohit Sachdeva, Plano, TX (US); Rüdger Rubbert, Berlin (DE)

(73) Assignee: Orametrix, Inc., Richardson, TX (US)

( * ) Notice: Subject to any disclaimer, the term of this patent is extended or adjusted under 35 U.S.C. 154(b) by 532 days.

This patent is subject to a terminal disclaimer.

(21) Appl. No.: 11/074,423

(22) Filed: Mar. 8, 2005

(65) Prior Publication Data

US 2005/0153255 A1    Jul. 14, 2005

Related U.S. Application Data

(60) Division of application No. 10/137,495, filed on May 1, 2002, now Pat. No. 7,160,110, which is a continuation-in-part of application No. 09/835,039, filed on Apr. 13, 2001, now Pat. No. 6,648,640, which is a continuation-in-part of application No. 09/560,640, filed on Apr. 28, 2000, now abandoned, and a continuation-in-part of application No. 09/451,609, filed on Nov. 30, 1999, now Pat. No. 6,250,918.

(51) Int. Cl.
*A61C 3/00* (2006.01)
*A61C 11/00* (2006.01)
*A61C 13/00* (2006.01)
*A61C 5/08* (2006.01)

(52) U.S. Cl. .................. 433/24; 433/213; 433/167; 433/218

(58) Field of Classification Search ................. 433/24, 433/167, 213, 218
See application file for complete search history.

(56) References Cited

U.S. PATENT DOCUMENTS 5,338,198 A * 8/1994 Wu et al. ................. 433/213
6,318,994 B1 * 11/2001 Chishti et al. ............. 433/24
6,739,869 B1 * 5/2004 Taub et al. ................ 433/24

FOREIGN PATENT DOCUMENTS

WO    WO 98/52493    * 5/1998

* cited by examiner

*Primary Examiner*—John J Wilson
*Assistant Examiner*—Heidi M Eide
(74) *Attorney, Agent, or Firm*—McDonnell Boehnnen Hulbert & Berghoff LLP

(57) ABSTRACT

Occlusal contact between upper and lower virtual three-dimensional teeth of a patient when the upper and lower arches are in an occlused condition are determined and displayed to the user on a user interface of a general purpose computing device. Various techniques for determining occlusal contacts are described. The areas where occlusal contact occurs is displayed on the user interface in a readily perceptible manner, such as by showing the occlusal contacts in green. If the proposed set-up would result in a interpenetration of teeth in opposing arches, such locations of interpenetration are illustrated in a contrasting color or shading (e.g., red). The ability to calculate distances and display occlusal contacts in a proposed set-up assists the user in planning treatment for the patient. The process can be extended to interproximal contact detection as well. The concepts also apply to dental prosthetics, such as crowns, fillings and dentures.

17 Claims, 4 Drawing Sheets

THREE-DIMENSIONAL OCCLUSAL AND INTERPROXIMAL CONTACT DETECTION AND DISPLAY USING VIRTUAL TOOTH MODELS

CROSS-REFERENCE TO RELATED APPLICATIONS

This application is a divisional application of U.S patent application Ser. No. 10/137,495 filed May 1, 2002, now U.S. Pat. No. 7,160,110, which is a continuation-in-part of U.S patent application Ser. No. 09/835,039 filed Apr. 13, 2001, now U.S Pat. No. 6,648,640, which is a continuation-in-part of U.S patent application Ser. No. 09/560,640 filed Apr. 28, 2000, now abandoned, and Ser. No. 09/451,609 filed Nov. 30, 1999, now U.S Pat. No. 6,250,918. The entire contents of each of the related applications and patents is incorporated by reference herein.

BACKGROUND OF THE INVENTION

A. Field of the Invention

This invention relates generally to the fields of dentistry and orthodontics. More particularly, the invention relates to methods for evaluating the areas of contact, and near contact, between upper and lower teeth when the upper and lower arches are in a closed or occluded condition. Knowledge of such areas of contact ("occlusal contacts" herein) is helpful in planning orthodontic treatment. The present invention provides methods of determining and displaying such occlusal contacts using a computer and three-dimensional virtual models of teeth.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. Corrections to the bracket position and/or wire shape are made manually by the orthodontist.

The key to efficiency in treatment and maximum quality in results is a realistic simulation of the treatment process. Today's orthodontists have the possibility of taking plaster models of the upper and lower jaw, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per jaw that covers all brackets and relevant portions of every tooth. Using such a transfer tray guarantees a very quick and yet precise bonding using indirect bonding.

However, it is obvious that such an approach requires an extreme amount of time and labor and thus is too costly, and this is the reason why it is not practiced widely. The normal orthodontist does not fabricate set-ups; he places the brackets directly on the patient's teeth to the best of his knowledge, uses an off-the-shelf wire and hopes for the best. There is no way to confirm whether the brackets are placed correctly; and misplacement of the bracket will change the direction and/or magnitude of the forces imparted on the teeth. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. And the patient has no choice and does not know that treatment time could be significantly reduced if proper planning was done.

U.S. Pat. No. 5,431,562 to Andreiko et al. describes a computerized, appliance-driven approach to orthodontics. In this method, certain shape information of teeth is acquired. A uniplanar target archfoirn is calculated from the shape information. The shape of customized bracket slots, the bracket base, and the shape of an orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, in the late 1990's Align Technologies began offering transparent, removable aligning devices as a new treatment modality in orthodontics. In this system, a plaster model of the dentition of the patent is obtained by the orthodontist and shipped to a remote appliance manufacturing center, where it is scanned with a laser. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position. Representative patents describing the Align process include U.S. Pat. Nos. 6,217,325; 6,210, 162; and 6,227,850, which are incorporated by reference herein.

Other patents addressed to planning treatment for a patient include Doyle, U.S. Pat. No. 5,879,158, Wu et al., U.S. Pat. No. 5,338,198 and Snow et al., U.S. Pat. No. 6,068,482.

Orthodontics and dentistry involves the three-dimensional spatial positioning of teeth to get the best possible fit. Critical to the success is the relative position of the teeth within the arch and with the opposing arches. The determinants of these relationships is driven by both the location and shape/form of the teeth. Although teeth may be ideally localized spatially their fit may be poor because the shape of the teeth is improper. Determination of the fit between teeth can be best estimated by defining the contact points/areas between them.

Therefore, if the teeth are located correctly and the contact points are not, it may be assumed there are discrepancies in the shape of the teeth. Location of these discrepancies is vital to achieve the desired occlusion.

Present approaches to defining or identifying these discrepancies are at best empirical. In current orthodontic and dental practice, occlusal contacts are determined by an orthodontist or dentist by using a color coated, thin plastic sheet known as "articulating paper". The patient "bites" onto this foil, and the color is transferred onto the tooth surface, thus indicating where teeth have occlusal contact. This technique is contact-based and provides no quantitative data in terms of degree of poor fit.

In accordance with one aspect, the present invention provides for a simulation of this determination and display of occlusal contact using computer techniques and a virtual model of the patient's dentition. The determination and display of the occlusal contacts during treatment planning, prior to initiating treatment, allows for the orthodontist to better optimize the set-up on the computer. For example, the orthodontist may realize that the set up should be modified by moving one or more teeth relative to the opposing arch to provide for better occlusal contact or prevent a collision between teeth during movement of the teeth from initial to finish positions. Once this more optimal tooth set up has been determined an appliance to move teeth to the desired positions can be designed and fabricated. The present invention is applicable to appliance systems generally and is not limited to a bracket and wire approach to straightening teeth.

SUMMARY OF THE INVENTION

In a first aspect, a method is provided for determining the proximity of teeth of upper and lower jaws of a patient. The method includes the steps of:
   a) storing data representing three-dimensional models of teeth from the upper and lower arches of the patient in a memory associated with a computer; and
   b) determining, with the computer and the models, distances between surfaces of teeth in one of the upper and lower arches and surfaces of teeth in the other of the-upper and lower arches when the teeth of the arches are in an occluded condition representing an occlusion of the patient. Various possible methods for determining the distances between surfaces of the teeth in the upper and lower arches are contemplated and described in detail below.

From these measurements of distances, it is possible to determine the locations on the tooth surfaces where the teeth are in contact, where the teeth are nearly in contact, and where one or more teeth from one arch may intrude into a tooth or teeth in the opposite arch. For example, a contact may be defined as occurring when the distance between the surfaces is less than a predetermined threshold, such as 0.1 mm. Negative values of the distance can be associated with interpenetration or intrusions of one tooth into the opposite tooth.

Thee distance measurements can be assigned to the various locations on the tooth surfaces from which the measurements are taken. It is then possible to illustrate locations where contact occurs on a user interface, such as a computer workstation having a display screen. The workstation typically includes a treatment planning program that includes the occlusal contact determination feature. Thus, in a presently preferred embodiment, the method further comprising the steps of providing a user interface for displaying the three-dimensional models of the teeth, displaying all or a portion of at least one of the upper and lower arches on the user interface, and indicating on the models information associated with the calculations. For example, the areas where contact occurs can be illustrated in one color (e.g., green), and areas in which intrusion would occur can be illustrated in a second color (e.g., red). As an alternative, the distance calculations can be represented in tabular or other format as numerical distance information for selected portions of the teeth.

The orthodontist will typically perform the method of the present invention as one tool in evaluating a proposed set-up for the patient. Based on the measurements of distances between the teeth, and the possible presence of intrusions, he or she can operate the treatment planning software to move the teeth relative to each other to provide a more optimal set-up. Alternatively, the orthodontist may be satisfied with the set-up and can deal with the intrusions by grinding away a portion of one or the other tooth involved in the intrusion so as to eliminate the intrusion.

In another aspect, a method is provided for evaluating a proposed set-up of teeth in planning treatment for an orthodontic patient. The method comprises the steps of:
   a) obtaining a three-dimensional digital model of the teeth of the upper and lower arches;
   b) moving the digital models of the teeth to a proposed set-up for treating the patient;
   c) calculating distances between portions of the teeth in the upper and lower arches when the teeth are positioned in an occluded condition; and
   d) displaying the virtual models of the teeth to a user in a manner such that a user can readily distinguish portions of the teeth in the upper and lower arches in which the distance between the portions is less than a predetermined threshold.

Occlusal contact information can be determined statically, or dynamically. For example, in another embodiment of the invention the teeth are moved from an open to a closed condition and the initial areas of contact are determined and displayed. As another example, the occlusal contacts can be determined by simulating a chewing motion of the upper and lower arches and calculating distances between the teeth during the chewing motion to find the areas of contact between the upper and lower arches.

As another embodiment of the invention, the feature of determining distances between teeth and displaying such information can be used to determine interproximal points of contact. The feature can be extended to determining interproximal and occlusal contact for virtual prosthetic devices, such as crowns and bridges. The determination of such contacts on a compute allows the clinician to evaluate the prosthetic device and optimize its shape, position and/or orientation so as to maximize its interproximal and occlusal relationship to adjacent and opposing teeth.

In still another aspect, the use of contact information can enable a "magnetic" function by which teeth are automatically positioned in close proximity or touching contact with an adjacent tooth or an opposing tooth. In particular, a method is provided of manipulating virtual teeth on a user interface of a general-purpose computer, the user interface including a display and a pointing device. The virtual teeth includes a first virtual tooth and a second virtual tooth, the second virtual tooth comprising either an adjacent tooth or an opposing tooth of the first virtual tooth. The method includes the steps of selecting the first virtual tooth with the pointing device, moving the pointing device while the first virtual tooth is selected so as to drag the first virtual tooth in the direction of the second virtual tooth, automatically moving the first virtual tooth so as to place the first virtual tooth into proximity with the second virtual tooth without requiring said user to drag the first virtual tooth into proximity to the second virtual tooth. This feature simulates a magnetic attraction of the first virtual tooth to the second virtual tooth. The feature makes design of a proposed set-up for the patient easier and less time consuming.

These and many other aspects and features of the various inventions disclosed and claimed herein will be explained in more detail in the following description of a presently preferred implementation.

BRIEF DESCRIPTION OF THE DRAWINGS

Presently preferred embodiments of the invention are described below in conjunction with the appended drawing figures, where like reference numerals refer to like elements in the various views, and wherein.

DETAILED DESCRIPTION OF PREFERRED EMBODIMENTS

Overview

Figure 1:
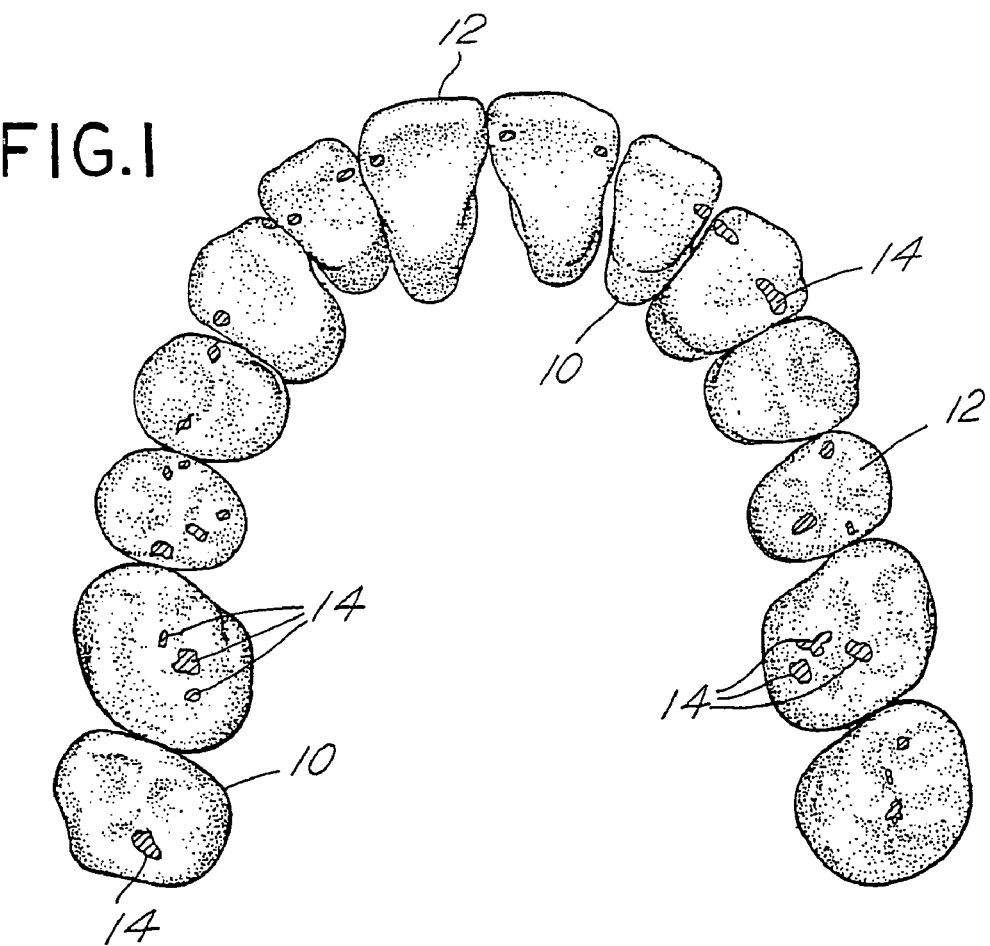
FIG. 1 is a view of a set of virtual three-dimensional tooth models representing the teeth of the lower arch of a patient, as they might be presented on the screen of a computer. The teeth have been moved from a maloccluded condition to a proposed set-up or finish position using a treatment planning program. The portions of teeth that would have occlusal contact with the teeth on the upper arch are shown in a contrasting color or shading to assist the orthodontist in evaluating the proposed set-up.

The determination and display of occlusal contacts between teeth in the upper and lower jaws in accordance with a preferred embodiment of the invention makes use of three-dimensional virtual models of teeth. The virtual models of teeth are stored in a memory and available to a general-purpose computer. As is known in the art, virtual models of teeth of a patient can be obtained by using a laser scanner to scan a physical model of the dentition. Alternatively, the teeth can be scanned in vivo, or a model of the dentition can be scanned, by a hand-held scanner such as the type described in published PCT application of OraMetrix, Inc., PCT/US01/11969, publication no. WO 01/80761, the entire contents of which is incorporated by reference herein.

Once the teeth have been scanned, the three-dimensional scan data can be represented in a a computer and displayed to the user as a three-dimensional model. There are a variety of techniques known in the CAD/CAM art for representing a three-dimensional surface, and the choice of a particular technique or format for representation of the virtual teeth is not important. The present invention will be described in context of a representation of a surface as a set of points that define contiguous three-dimensional triangular shaped surface segments. Other representations of a surface such as Nonuniform Rational B Splines (NURBS) can be used. A volumetric description using voxels (a technique known in the art) automatically describes a surface and that is another possibility.

After the dentition, or a physical model of the dentition, has been scanned, it is helpful to separate the individual teeth from the rest of the anatomical structures (e.g., gingival tissue) so that individual teeth can be represented as independent, individual three-dimensional virtual objects. This is described in the above-referenced PCT application of OraMetrix. Once the teeth have been separated into such individual objects, CAD/CAM techniques can be used to move the teeth relative to each other to arrive at a set-up for the patient. A particularly advanced and highly preferred treatment planning software application that performs these and other tasks is described at length in the above-referenced PCT application of OraMetrix. The software preferably provides the user with the ability to display the arches individually, or together, either alone or in an occluded condition. The relative position of the arches in the occluded position is preferably user-specified by the treatment planning software. Since the techniques used to moved teeth and/or arches relative to each other are already described in the patent literature, the details are omitted from the present discussion for the sake of brevity.

As noted above, once the teeth are represented as virtual objects and moved to a proposed set-up representing an ideal archform for the patient, it is possible to evaluate the set-up under a variety of criteria, prior to initiating treatment. One possible criteria for evaluation is the occlusal contacts. The present method of determining and displaying occlusal contact information preferably involves measuring the distance from the teeth in one arch to the teeth in the other arch, with the arches in an occluded condition. More particularly, the method involves measuring or determining the distance between a plurality of locations (points or surfaces) of one tooth and the closest locations (i.e., surfaces or points) of teeth in the opposite arch.

In a preferred implementation, for each point (vertex) of the surface of the digital tooth model, the closest surface point of an opposing tooth is determined. The distance can be calculated using the computer, since the relative positions of the teeth of both arches in three-dimensional space is known and stored in the computer. Once the distance has been calculated, the tooth surfaces in which the distance is less than a predetermined threshold can be illustrated or displayed to the user in a manner that allows the user to readily perceive such locations. For example, the tooth surfaces which are less than 0.1 mm apart are deemed to be "occlusal contacts" and are colored or given a shading. In an example in which the surface of the teeth is represented a contiguous triangle surfaces, we can assign a color (e.g., green) or a particular type of shading to the triangles that are associated to the point or surface at which the distance was calculated and the minimum distance to the opposite tooth is less than the threshold.

FIG. 1 shows a three-dimensional virtual model of the teeth of the patient, consisting of individual and independently moveable tooth objects or teeth 10, which have been moved by a treatment planning software application to a proposed set-up. The teeth include cusps 12. The distance between locations on the surface of the teeth in the lower arch to the teeth in the upper arch has been performed when the virtual model of the upper and lower arches are moved to an occluded position. The distances which are less than a threshold value, such as 0.45 mm, are shown on the monitor of the workstation in a contrasting color or shading as occlusal contact regions 14.

In one possible embodiment, it is possible to use a smooth transition of tooth color to green. Points that are further away than 0.45 mm from the opposing tooth are colored purely in tooth color. Points that contact the opposing tooth are colored in pure green. All other points receive a color that is between tooth color and green, according to the distance. Thus, we have a continuous transition from tooth color to green. The granularity of this transition may be limited depending on the typical size of the triangles defining the surface, and the abilities of the rendering engine software that is being used to display those triangles at the computer monitor. Some rendering engines do not allow definition of colors within a triangle, but rather it is only possible to define colors for the vertex points defining a triangle and the rendering engine will then color the triangle accordingly. However, if we had a finer triangle resolution, we would have a very smooth transition from tooth color to green.

Figure 2:
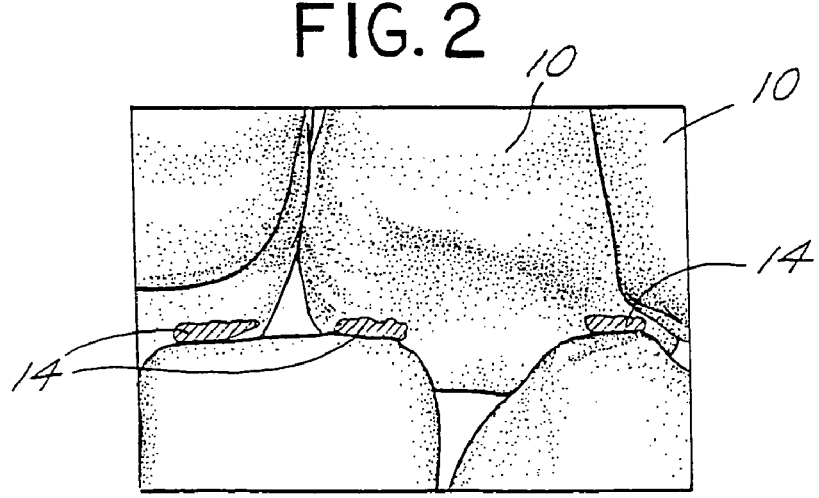
FIG. 2 is another view of a portion of the upper and lower arches of the patient in the proposed set-up, with the view taken from the lingual side of the arches, showing the spatial relationship of the teeth of the upper and lower arches with the occlusal contacts on the teeth of the upper arch shown in a contrasting color or shading

FIG. 2 shows another view of the upper and lower arches in the occluded condition, with the occlusal contacts shown as regions 14.

One possible color scheme for representing the occlusal contacts is as follows. If the distance between the opposing tooth and the point or portion of the tooth to be examined is smaller than 0.45 mm, the area 14 is shaded green. The value of 0.45 is somewhat arbitrary, and preferably can be user specified by modifying a variable in a suitable screen of the treatment planning program. The smaller the value is, the smaller the area displayed as occlusal contact would be. Since, mathematically speaking, only one point really contacts the opposing tooth, we would only have tiny dots if we would indicate only points that actually have contact. The value of 0.45 mm has been found to provide a more useable result.

If the distance is negative, this would indicate interpenetration, that is, a portion of one tooth has collided with the opposing tooth such that it physically projects into the other tooth. This is an undesirable outcome when planning treatment, clinically speaking. Thus, when an orthodontist is planning treatment and evaluating a proposed treatment plan, whether or not such interpenetration between teeth of opposing arches would result is of great interest to the orthodontist.

Figure 3:
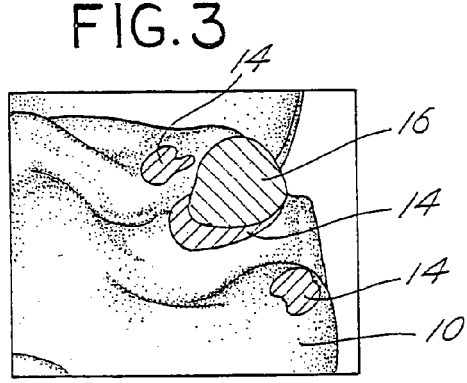
FIG. 3 is a view of a molar of a virtual three dimensional tooth with one portion of the tooth cusp shown on one color (e.g., green) to show areas which are occlusal contact with the opposite tooth and another portion shown in a second color (e.g., red) showing areas in which the opposite tooth would interpenetrate the tooth in the proposed set-up, thereby indicating the need to revise the treatment plan.

The present method enables such situations to be determined and displayed to the user. For example, we can show such interpenetration or negative distance values, using a red color to indicate the affected tooth portions. In FIG. 3, the molar 10 has occlusal contact portions 14 and a region 16 shown in red which would be penetrated by the opposite tooth-in the other arch should the proposed treatment plan be implemented and an occlusion occur. Obviously, this is undesirable since in reality teeth cannot penetrate each other. Such a se-up would therefore represent an unrealistic scenario. The red region 16 thus alerts the orthodontist to the problem. The problem can be corrected by adjustment of the plan by simulation of movement of the affected tooth or teeth relative to each other to eliminate the interpenetration or by grinding the affected portions of the tooth or teeth.

When operating the treatment planning software for a patient with a malocclusion, the software is developed such that the user is normally prevented from moving teeth into one another when designing a tooth finish position. However, sometimes teeth have features that may need to be ground by the orthodontist to receive good occlusion. In such a case, the treatment planning software allows the user to override the interpenetration prohibition feature, so that the user can indeed move teeth into one another. The red spot 16 of FIG. 3 representing an interpenetration tells the orthodontist very clearly and exactly, which portion has to be ground away. The orthodontist can do this at a very early state of treatment. This is an advantage, since we allow the teeth to readily move into the desired occlusion once a disturbing feature is ground, instead of waiting and finding out very late that grinding is required.

In a possible alternative implementation, the software virtually "subtracts" or deletes the opposing tooth from the tooth to be ground to thereby modify the three-dimensional virtual form of the tooth to be ground. This subtraction or deletion can be done using known CAD/CAM techniques. The modified tooth shape is then displayed to the user. This procedure allows the orthodontist to determine exactly not only which area needs to be ground, but to which shape. In yet another implementation, the orthodontist grinds the tooth carefully, scans it, compares the scan data to the shape of the modified virtual tooth model, and thus determines whether and where further grinding is required.

Preferred Implementation of Contact Detection

Figure 4:
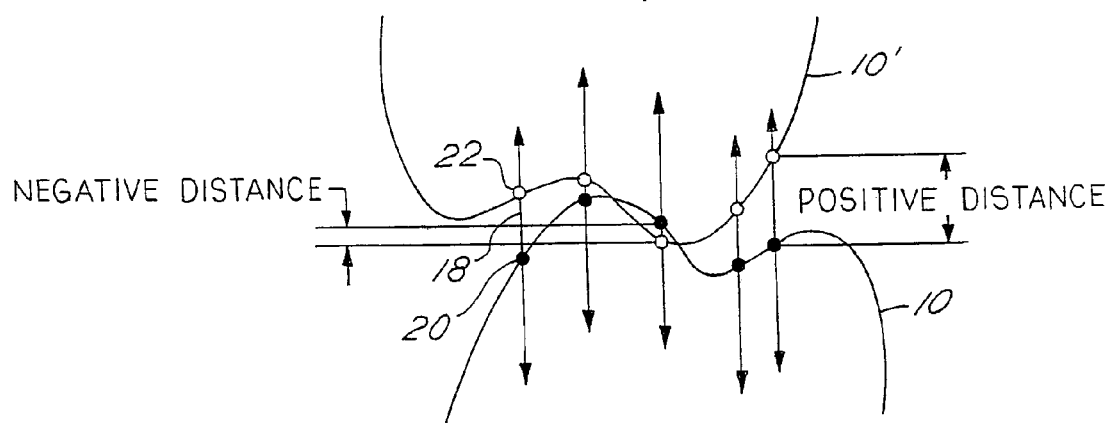
FIG. 4 is a schematic representation of a tooth in the upper and lower arches, illustrating one method to determine the distance between portions of the teeth.

There are several ways to determine occlusal contacts. We have preferred a simple and fast approach, which is as follows. With reference to FIG. 4, from each vertex point 20 (corner point of a triangle making up one element of the surface), a ray or vector 18 is constructed running along a pre-defined direction. In a preferred implementation, this direction is parallel to the tooth axis, which is defined for each tooth as a central axis extending the length of the tooth through the center of the cusp. Other options are discussed further below. Each ray 18 is sent both to the outside and the inside of the tooth, as shown in FIG. 4. Then, we determine where the vector intersects the surface of opposing teeth 10'. These points of intersection (actually, small triangle surfaces) are shown as points 22 in FIG. 4. The distance from the vertex point 20 to the intersection 22 is calculated. According to the color scheme, the triangles associated to the vertex point 20 are assigned a color depending on the distance and the mathematical sign (positive/negative). For example, the surfaces associated with vertex point 20 with a negative value are colored red. All surfaces 20 with a positive value less than 0.45 mm are colored green. The surface where the distance is greater than or equal to 0.45 mm are not colored. The virtual models of the upper and lower arches are displayed (typically separately) with the color information on a user interface of the workstation implementing the program. See, for example, the views shown in FIGS. 1-3.

This procedure is performed for every surface element (triangle) of the tooth. The procedure is also done for each tooth in one of the two arches. In one possible embodiment the user is able to modify the separation distance variable that is indicative of an occlusal contact (e.g., 0.45 mm). Alternatively, the separation distance can be programmed as a fixed parameter.

Figure 5:
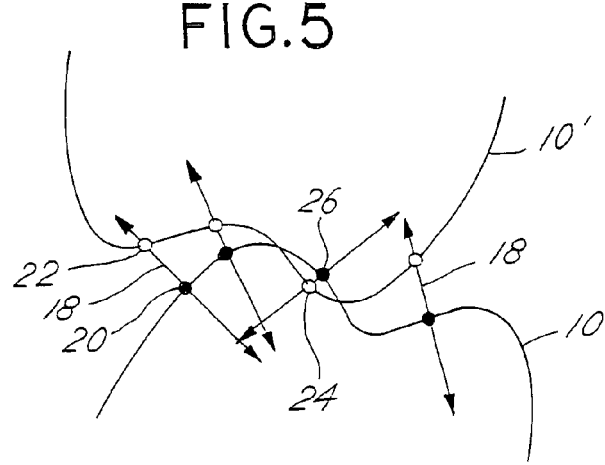
FIG. 5 is a schematic representation of a tooth in the upper and lower arches, illustrating an alternative method to determine the distance between portions of the teeth.
Figure 6:
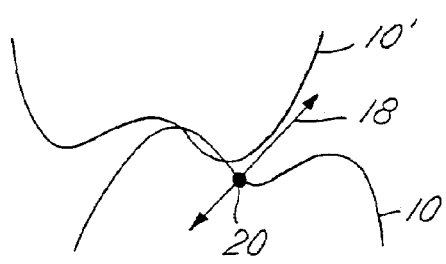
FIG. 6 is a schematic representation of a tooth in the upper and lower arches, illustrating one of the disadvantages to the method of FIG. 5.

We have selected the approach of FIG. 4 because it is very fast, computationally speaking. An alternative, more sophisticated approach would be to send the rays in the direction of a normal vector to the tooth surface. This is shown in FIG. 5, where the rays 18 are directed normal to the tooth surface 10. This alternative would require more time, since the normal vectors 18 of FIG. 5 would have to be calculated for each vertex point. However, since there is no normal vector to a point, we would have to calculate the normal vector to each triangle surface element that the vertex belongs to, and then calculate the median vector. The preferred embodiment described in conjunction with FIG. 4 avoids these additional computational steps and thus is quicker to perform using a state of the art microprocessor. As processing speeds improve, the alternative method of FIG. 5 may become perfectly suitable and thus may represent a better and more accurate alternative. Additionally, the process of FIG. 5 may not by default create better results, as is shown in FIG. 6. Here, the normal vector 18 from point 20 barely misses the tooth surface 10', whereas the method of FIG. 4 would have definitely located the surface immediately above the point 20.

Figure 7:
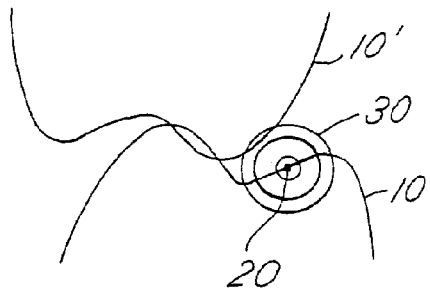
FIG. 7 is a schematic representation of a tooth in the upper and lower arches, illustrating an alternative method to determine the distance between portions of the teeth.

An ideal method for determining the closest surface of the opposite tooth is shown in FIG. 7. The method involves creating a virtual sphere 30 around each point in the tooth 10, and increasing the diameter D of the sphere in suitable increments (e.g., 0.01 mm) until the sphere intersects with an opposing surface. The value of D then indicates the proximity of the point of the tooth with the opposite tooth and this value is stored for the point. The process is done for all the points comprising the tooth surface. The treatment planning software then displays the model of the teeth with all surfaces corresponding to the points for which 0<D<0.45 mm displayed in green, and all surfaces corresponding to the points for which D<0 displayed in red.

The algorithms described thus far are applicable approaches for three-dimensional virtual objects that have a surface representation created by vertex points and connecting surface elements (triangles etc.). However, there are other acceptable mathematical techniques for representing arbitrary three-dimensional shapes in a computer. The techniques include volumetric descriptions (IGES format), and Nonuniform Rational B Splines (NURBS). These techniques could be used. A person skilled in the art would not have difficulty to design an appropriate algorithm for determining occlusal contacts using these or other techniques.

Figure 8:
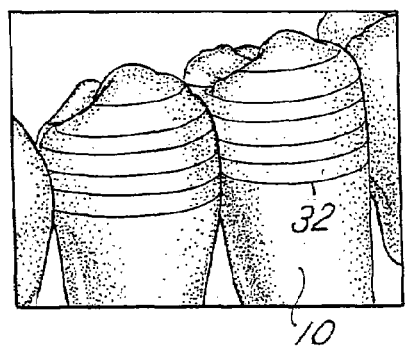
FIG. 8 shows a set of teeth in one arch with parallel planes intersecting the teeth to form parallel lines, illustrating one technique for determining the closeness of teeth; the parallel lines can be created vertically to determine the separation between teeth in the upper and lower arches.
Figure 9:
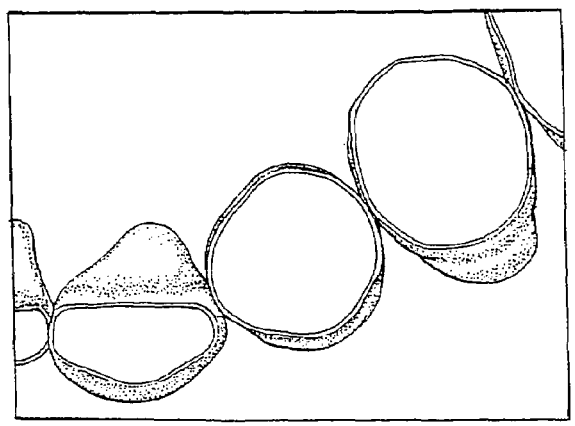
FIG. 9 is a cross-section through the teeth of FIG. 8 along one of the planes illustrated in FIG. 8.

One example would be the "contour line" algorithm, which will be described in conjunction with FIGS. 8 and 9. At the tooth surface, contour lines 32 are calculated in predefined planes (e.g. 0.1 mm). FIG. 9 is a cross-section through the teeth along one of the contour lines 32. Within each plane, such as shown in FIG. 9, a check is performed to see if contour lines of adjacent teeth intersect. This approach could also be used to detect occlusal contacts. In particular, a set of parallel planes are defined that are oriented in a vertical direction instead of a horizontal direction. The planes will intersect the surfaces of the upper and lower teeth, thereby forming two lines on each plane, one for the tooth in the lower arch and the other for the tooth in the upper arch, analogous to the lines shown in the cross section of FIG. 9. The software then looks for areas in which the separation distance between the two lines is less than a threshold. If the two lines intersect, the teeth touch. If a bounded or closed volume is formed by the two lines, then an interpenetration of the teeth has occurred. The contour line algorithm can be used with any kind of 3D object description. The technique of FIG. 9 can be used to determine the interproximal distances between teeth, as discussed further below.

Another possible embodiment uses an "octree" data structure (a known technique) to describe the shape of teeth. This further eases the task of contact detection, since the data is organized in spatial cells and the amount of data needed to represent the surface is reduced significantly, resulting in reduced time to calculate occlusal contacts.

Figure 10:
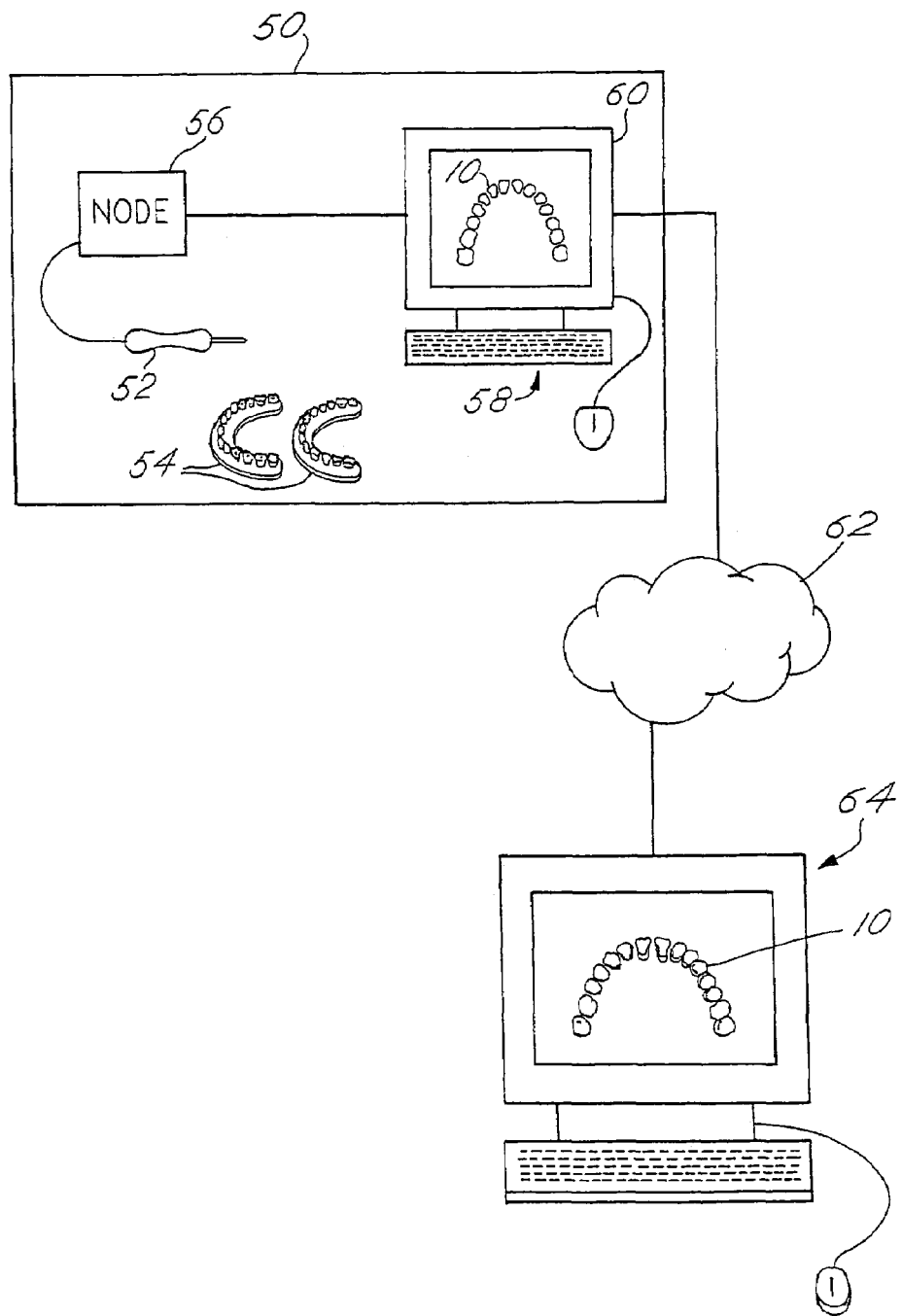
FIG. 10 is an illustration of a scanner and computer system that can be used, in the practice of the present invention.

One possible computer and scanner arrangement for practicing the invention is shown in FIG. 10. An orthodontic clinic 50 is equipped with a hand-held scanner 52 which is used for either in-vivo scanning of a patient or scanning a physical model 54 of the upper and lower arches. The hand-held scanner 52 supplies scan data to a scanning node or computer 56 which processes the scan data to derive three-dimensional shape data from the arches. This data is supplied to a general-purpose computer 58 having a user interface 60. The computer 58 is equipped with or accessible to a memory (not shown) storing the tooth models and an interactive treatment planning software. The software separates the individual teeth from the surrounding anatomical structures and allows the user to interactively and selectively move the teeth to a desired dental archform for both upper and lower arches. One possible embodiment of a scanner and workstation providing treatment planning software for virtual teeth of the upper and lower arches is described in the PCT application of OraMetrix, Inc., referenced previously. The workstation also includes occlusal contact and detection tools as described above that allow the orthodontist to view the virtual teeth 10 on the workstation with the occlusal contacts illustrated in a contrasting color (such as red or green).

The workstation or computer 58 is shown coupled via the Internet 62 to a remote facility having an orthodontic server 64. In one possible embodiment, the scan data from the scanner 52 is sent to the remote facility and the orthodontic server 64 generates an initial treatment plan for the orthodontist to review. The occlusal contact detection and display can of course occur at the orthodontic server. Similarly the virtual model of the teeth may be sent electronically to other locations and shared and viewed by other health care professionals that are treating the patient.

The collision or contact detection features described above enable another useful feature in planning treatment for a patient. This additional feature is that when one virtual tooth is moved to a new location, the tooth is automatically moved into close proximity or touching contact with the adjacent or opposite tooth. This feature streamlines the process of designing proposed set-ups for a patient, as it keeps all the teeth together and places them in contact in the arch. This technique is referred to herein as a "magnetic" function.

The collision detection/prevention functionality is possible due to a feature of the Windows® operating system. Whenever the mouse is moved, the operating system not only places the mouse pointer at the respective location at the screen. It also sends a message to the program that owns the window where the mouse pointer is currently being moved over. This message is sent over and over, as long as the mouse is on the move. The message includes the current location of the mouse pointer. The same thing happens (obviously only once), when you click the mouse or release the mouse. This functionality is a fundamental aspect of 3D software running on a Windows® operating system. In our implementation, the user clicks the mouse. We store the respective location of the mouse pointer. The user moves the mouse. The operating system continuously sends messages containing the current location of the mouse pointer. Our presently preferred treatment planning software calculates the distance that the mouse pointer has covered and the direction, and we then move the 3D object that is currently selected respectively, and immediately display the new location on the screen. This is one way how the user can move a virtual object such as a tooth. However, before simply moving the object in accordance with the mouse movements, we can perform any kind of calculations, such as distance calculations to opposing or adjacent teeth. If the collision prevention feature is enabled or active, we calculate the remaining distance to the opposing (or adjacent) tooth. If this distance is smaller than the distance that the user indicated by mouse movement, we simply move the object only according to the remaining distance. To the user, this looks as if the object is hitting the opposing or adjacent object and cannot move any further.

When the magnetic functionality is activated, and the user has selected a tooth and starts moving it by dragging with the mouse, we calculate the remaining distance to the opposing tooth and immediately move the tooth over the complete distance, no matter how far the mouse has really been moved. So the selected tooth will immediately get in contact with its opponent. This calculation is performed on all mouse movements, whether they indicate translations or rotations. The distance between the selected tooth and its opponent is kept to zero, so that the tooth appears to be "magnetically" attached to its opponent. Alternatively, the tooth could be placed in close proximity, that is, separated by some amount such as 0.01 mm. In one possible embodiment, the user is allowed to modify the separation distance, such as by clicking on a suitable icon and selecting a new value for the separation distance.

Other embodiments and Features

A. Initial Occlusal Contact Determination and Occlusal Contact Determination During Treatment The occlusal contact determination can be made for the initial (maloccluded) condition of the patient's teeth. The patient's teeth are scanned (either directly or from a physical model) and then the scan data is converted into a 3D representation of the dentition. A bite registration scan is performed, and the three-dimensional relationship of the upper and lower arches of the teeth is obtained. The virtual models of the upper and lower arches can now be positioned in an occluded condition and the process described above can be performed to find the occlusal areas.

The identification and display of the occlusal contacts in the initial condition is helpful in evaluating a proposed treatment plan because it enables the practitioner to compare the initial and proposed treatment plans in terms of occlusal contacts. For example, the user interface could be organized into a split screen to show the occlusal contacts for the lower jaw in the initial condition on the left hand side and the occlusal contacts in the proposed treatment on the right hand side of the screen.

The determination of occlusal contacts can also be obtained and displayed at any time during treatment. During treatment, the upper and lower arches are scanned and a bite registration scan is taken. Preferably, for a bracket and wire type of treatment regime, the scans are performed in vivo using a hand-held 3D scanner such as described in the published PCT patent application of OraMetrix, Inc. cited previously. Again, a qualitative assessment of the occlusal contacts can be made to more completely assess the progress of treatment, and the current stage of occlusal contacts can be compared to the expected treatment outcome and initial occlusal contacts to verify that the treatment is progressing properly. In the event that the occlusal contact detection and display results in a desire to change the treatment, the treatment plan can be revised and the patient fitted with a modified orthodontic appliance. For example, the wire may be given a modified geometry to move the teeth into a more optimal position to increase the occlusal contact area.

B. Dynamic Detection of Occlusal Contacts

The present invention also provides for the ability to determine and display occlusal contacts dynamically, that is, the order and location at which the contacts occur when the patient's jaw are moved dynamically from an open to a closed condition. The 3D models of the upper and lower arches can be moved relative to one another to simulate closing of the jaw or a chewing motion. This simulation can be done for initial condition of the arches, or for the arches when the teeth are moved relative to each other in a proposed treatment plan. The dynamic model of the motion of the mandible relative to the maxilla during occlusion or chewing can be obtained via a variety of imaging techniques, including video, X-ray, or successive scans of the upper and lower arches as the patient moves their teeth. The determination of where the teeth are coming into contact during an occlusion or during a chewing motion yields clinically important information that is helpful in planning treatment, revising an initial treatment plan, or in consideration of whether additional medical care is recommended for the patient.

Thus, in another aspect, a method is provided for determining the proximity of teeth of upper and lower jaws of a patient comprising the steps of:
  a) storing data representing a three-dimensional model of teeth from the upper and lower arches of the patient in a memory associated with a computer;
  b) simulating motion of said upper and lower arches relative to each other; and
  c) calculating, with said computer and model, distances between surfaces of teeth in one of said upper and lower arches and surfaces of teeth in the other of said upper and lower arches during said simulation of motion.

Information regarding the calculations can be illustrated to the user on a display associated with the computer, such as showing the initial contacts in one color, and all of the other occlusal contacts in a contrasting color or shading. The display of contact information can be a static display of the teeth or in a dynamic simulation of the motion.

C. Tooth Wear and Occlusal Contact Monitoring

Many persons suffer from bruxism, a condition in which they grind their teeth, typically while they are asleep. Over time, the tooth enamel is worn down, which can lead to other problems for the patient including decay or disease of the tooth. Detection and monitoring of tooth wear is an important diagnostic feature provided in one aspect of the present invention.

The progress of the bruxism can be monitored by taking a scan of the patient initially, taking a second scan at a later point in time, and comparing the tooth models of selected teeth or all the teeth before and after. For example, a subtraction feature is employed by which the virtual model of a tooth at the later stage is subtracted from the model at the initial stage, with the difference being the portion of the tooth that has been worn away. A method of monitoring tooth wear is thus provided, comprising the steps of obtaining a first three-dimensional virtual model of a portion of the patient's dentition at a first point in time, obtaining a second three-dimensional virtual model of said portion of the patient's dentition at a second, later point in time; and comparing said first and second virtual models to each other. The step of comparison can be a subtraction operation, which is typically provided in CAD/CAM software. The method continues with the step of identifying, from step of comparison, portions of the first three-dimensional virtual model that are no longer present in said second three-dimensional model due to wear of the dentition. For example, the identifying step could be performed by illustrating on the display screen the first three-dimensional model with the areas worn away in a contrasting color or shading.

Alternatively, tooth wear can be monitored by measuring occlusal contacts at two different points in time. By measuring the occlusal contacts of the teeth both at an initial stage of treatment and at a later point in time, the occlusal contact areas can be compared to each other. One would typically expect that the occlusal contact surface area would increase in time, particularly in the areas where bruxism is occurring. The evaluation of before and after occlusal contacts can be made qualitatively, using a subjective visual assessment of the occlusal contacts as displayed on a monitor, or it can be done quantitatively. For quantitative occlusal contact analysis, measurement tools such as fine grid can be placed over the region of the occlusal contacts and the surface area of the occlusal contact measured or calculated either by a human operator or automatically using the computer.

The process can be extended to measurement of gingival recession and erosion caused by tooth brushing or chemical erosion.

D. Contacts Between Teeth

The distance detection algorithms described herein can also be used to determine the interproximal contact points between teeth, either in an initial situation or in a proposed treatment plan for the patient. Optimal interproximal contact points between teeth is important to avoid impaction of food between the teeth. The interproximal contact points can be identified by the algorithms explained previously for opposing teeth, except that the distance measurements are being made to the adjacent tooth. The technique of establishing parallel planes and determining where the planes intersect the teeth, as shown in FIGS. 8 and 9, yields a set of lines, one line for each tooth. The distance between the lines is indicative of the interproximal distance. This is a particularly useful approach. The interproximal contact points can then be displayed on the monitor of the workstation and evaluated by the user.

The ability to quantitatively measure and display interproximal contact points is a distinct advantage for an interactive treatment planning software program. In particular, it enables the user to position each tooth relative to its neighbor in a manner such that the interproximal contacts are optimized on a tooth by tooth basis. The treatment planning program preferably provides the orthodontist with the ability to move each tooth relative to another tooth, for example rotate about the tooth axis, tilt the tooth or move it up or down to optimize the interproximal relationship with the adjacent teeth. The visual display of interproximal contacts (such as in a green color where the separation distance is less than a threshold such as 0.1 mm) gives the user immediate feedback on the quality of the setup. Furthermore, as a given virtual tooth is moved, the software is preferably programmed such that the occlusal contact display changes immediately to give instant visual feedback as to the effect of tooth movement on occlusal contacts.

E. Restorative Dentistry and Dental Prosthetics

The occlusal contact and interproximal contact detection and display can also be a highly useful feature in planning restorative dentistry. For example, if no orthodontic treatment is planned but the patient is going to be given a crown, inlay, or other prosthetic device, the design and manufacture of the prosthetic device can be optimized in terms of providing interproximal and occlusal contact. This is achieved by scanning the patient's dentition, including a bite registration scan, and designing the shape of the prosthetic device as a virtual three-dimensional object on the computer. The design of the prosthetic device takes into account the interproximal (and occlusal) relationship to the other teeth. The three-dimensional shape of the prosthetic is optimized on the computer so that when it is implanted in the patient it achieves a superior interproximal and occlusal relationship with the rest of the patient's teeth.

In the specific case of crowns, crowns are typically made of gold using a lost wax process in a dental lab. The lost wax process includes an intermediate step of creating a wax model of the crown. The wax model can be scanned using a 3D scanner and the crown represented as an independent three-dimensional virtual object. The virtual object can then be fitted to a virtual model of the tooth, in effect simulating the installation of the crown in the patient. This simulation can occur in a workstation in the office of the dentist or in the lab. The dentist can evaluate the fit of the crown relative to the other teeth. If the dentist wishes to modify the shape of the crown, he or she can manipulate the model to add or subtract or otherwise modify the shape of the crown. The 3D model can then be exported to a rapid prototyping machine (such as, for example, stereolithography (SLA), laser 3D printing, etc.) for manufacture of a physical model of the crown. The process proceeds with a manufacture of a crown in gold or porcelain having the modified configuration.

The process can also be extended to fillings, namely the detection of occlusal contacts for filings and determination of high spots using the algorithms described herein. The challenge faced by the dentist is that as the filling is done the dentist asks the patient-to bite down to detect the high spot. Invariably, the pressure from the occlusion fractures the partially set amalgam. Our approach is a contactless approach and eliminates that risk. Similarly for crowns, our electronic detection eliminates any interventional episodes for chairside correction of the crown to ensure better fit.

Similar concepts apply when designing other appliances and prosthetic devices, such as dentures. The process of design can be carried out on a computer using virtual tooth models and the determination, display and evaluation of interproximal and occlusal contacts can be made on a workstation using the techniques described herein so as to optimize the design of the appliance or device.

The method can be extended to designing and fabricating a set of dentures for a patient and improving interproximal and occlusal contact of the teeth of the dentures. In this aspect, the method includes the steps of obtaining a three-dimensional virtual- model of teeth of upper and lower arches of the patient. This can be done for example using template teeth stored in memory (see the published PCT application of OraMetrix, Inc., cited previously) or from a scan of the patient's teeth. The virtual model is stored in a computer, preferably a computer having treatment planning software. The teeth of the upper and lower arches are moved relative to each other to a proposed arrangement for a set of dentures. Then, using the techniques described in detail herein, the computer calculates distances between surfaces of adjacent teeth and between surfaces of opposing teeth with the upper and lower arches in a closed condition to assess the interproximal relationship and occlusal contacts of the teeth. The computer displays information associated with calculations on a user interface, such as by showing occlusal contacts or interproximal contacts in a contrasting color or shading or using a transition from white to color. The dentist then uses the treatment planning software to adjust the position of one or more teeth to more optimally position of the teeth relative to each other as a result of the display of contact information. When the optimal arrangement is arrived at, the dentures are fabricated.

Not only can the above method be used for detecting denture contacts, it can be applied to surgical splints that are implanted in the patient's mouth. The design of the splint can be carried out on a computer and a milling machine can grind them accurately even before insertion.

F. Bracket, Wire, and Appliance Location and Conflicts

The above descriptions of occlusal and interproximal contact determination have assumed that one is measuring distance between teeth. The technique can be extended to determining distances between a tooth and a portion of an orthodontic appliance, such as a bracket or wire. The technique can also be used for determining the distance between opposing brackets in the upper and lower arches or between a bracket and an opposing wire, or between opposing wires. For example, the distance between a tooth cusp and the bracket on the opposing tooth is calculated using one of the algorithms described previously. The virtual models of the upper arches will be typically placed in a closed or occluded condition when this calculation is performed. The teeth and brackets are presented as virtual objects on the workstation of the computer with the areas in which the distance between the bracket and tooth is less than a threshold highlighted in a contrasting color or shading or as a smooth transition in color or shading. Actual collisions between the teeth and the brackets can also be calculated and displayed. This feature again helps the user evaluate a proposed treatment plan, including a proposed location of brackets on the teeth. The user is preferably able to modify the location of the virtual brackets on the teeth and run a new simulation of potential contact or collision between the appliance and the teeth. The collision or conflict detection process can also be performed based on actual location of the brackets on the patient's teeth, using a virtual model of the patient obtained from scanning of the patient.

Thus, in another aspect, a method is provided for determining potential conflicts in positioning of an orthodontic appliance on the dentition of the patient. The method comprises the steps of obtaining a virtual model of the upper and lower arches of patient's dentition; positioning a virtual model of an orthodontic appliance on at least one of the arches of the virtual model of the dentition; placing the virtual models of the upper and lower arches in an occluded condition; calculating distances between portions of the virtual model of the dentition and portions of the virtual model of the orthodontic appliance, and displaying the virtual models of the upper and lower arches and the orthodontic appliance on a user interface along with information associated with the calculations. The process can be extended to conflicts between brackets on opposing teeth, conflicts between brackets and gingival tissue, conflicts between brackets and wires in the opposing arch, and conflicts between upper and lower archwires.

Variations from the illustrated technique, methods and apparatus is contemplated without departure from the scope of the invention. The term "contrasting color or shading" in the claims in reference to the display of contact information, is intended to encompass the situation in which a transition of color occurs between portions of the tooth which are not contacts and portions which are (i.e. distance to the opposing or adjacent tooth is less than a threshold), as well as the situation in which no transition occurs and the portions below the threshold are illustrated in a contrasting color or shading and the portions above the threshold are illustrated in the usual manner (e.g., as white objects or in natural color). This true scope is to be ascertained by reference to the appended claims.

We claim:

1. A method of evaluating a proposed set-up of teeth in planning treatment for an orthodontic patient, comprising the steps of:

obtaining a three-dimensional digital model of the teeth of the upper and lower arches;

moving said teeth to a proposed set-up for treating the patient;

calculating distances between portions of said teeth in said upper and lower arches when said teeth are positioned in an occluded condition; wherein said step of calculating includes, for a plurality of points on a surface of a tooth, the step of calculating a sphere around each of said points, and enlarging the size of the sphere until the sphere intersects with a surface of a tooth on the opposing arch in said model; and displaying said teeth to a user in a manner such that said user can readily distinguish portions of said teeth in said upper and lower arches in which the distance between said portions is less than a predetermined threshold.

2. The method of claim 1, wherein said predetermined threshold is adjustable by the user.

3. The method of claim 1, wherein said portions of said teeth are displayed in a contrasting color relative to other portions of said teeth in which said calculations of distances results in distances greater than said threshold.

4. The method of claim 1, wherein said step of calculating results in a determination that a portion of a tooth of one of said arches intrudes into a portion of a tooth of the other of said arches, and wherein the method further comprises the step of displaying on a user interface the said portions of said tooth in a manner such that a user can readily distinguish said portions.

5. A machine for assisting a user in planning treatment for an orthodontic patient, comprising:

a central processing unit;

a user interface; and memory storing a set of instructions for said central processing unit and a data set representing a set of virtual teeth of a patient including the teeth of an upper arch and a lower arch;

said instructions comprising treatment planning software enabling a user to move the virtual teeth to a proposed set-up;

wherein said instructions further comprise a set of instruction for determining at least one occlusal contact of said upper and lower arches of said virtual teeth in said proposed set-up when said virtual teeth are in an occluded condition; wherein said set of instructions calculates a sphere around points on a surface of virtual teeth in one of said arches, and enlarges the size of said sphere until intersection of said sphere with a surface of a tooth on the opposing arch occurs thereby finding the separation distances between said virtual teeth in said opposing arches thereby enabling determining said at least one occlusal contact; and wherein said set of instructions includes instructions for display of said virtual teeth on said user interface with said occluded contact displayed in a manner readily observable to said user.

6. The machine of claim 5, wherein the proposed set-up would result in interpenetration of a tooth of one arch into a tooth of the opposing arch and said set of instructions displays on said user interface the location of said interpenetration in a manner such that a user can readily observe said location.

7. The machine of claim 5, wherein said set of instructions further comprises an instruction permitting the user to adjust a distance variable indicative of an occlusal contact.

8. The machine of claim 5, wherein said set of instructions includes a separation distance parameter indicative of an occlusal contact.

9. A method for determining the proximity of teeth of upper and lower jaws of an orthodontic patient, comprising the steps of:

a) storing data representing a three-dimensional model of teeth from the upper and lower arches of the patient in a memory associated with a computer;

b) simulating motion of said upper and lower arches relative to each other; and c) calculating, with said computer and model, distances between surfaces of teeth in one of said upper and lower arches and surfaces of teeth in the other of said upper and lower arches during said simulation of motion; wherein said step of calculating includes the step of calculating a sphere around a plurality of points on a surface of a tooth in said one arch of said model, and enlarging the size of the sphere until the sphere intersects with a surface of a tooth on the opposing arch in said model.

10. The method of claim 9, wherein said simulation of motion comprises a simulation of a closing of said upper and lower arches.

11. The method of claim 9, wherein said simulation of motion comprises a simulation of a chewing motion of said upper and lower arches.

12. The method of claim 9, further comprising the step of providing a user interface for displaying said three-dimensional model, displaying at least one tooth of said upper and lower arches on said user interface, and indicating on said display information associated with said calculations.

13. The method of claim 12, wherein said step of indicating comprises the step of displaying portions of said model in a contrasting color or shading relative to other portions of said model in which said distance between said portions is less than a predetermined threshold.

14. The method of claim 12, wherein said step of calculating results in a determination that the distances between portions of teeth in the upper and lower arches is less than or equal to zero, and wherein said portions are illustrated in a contrasting color or shading relative to other portions of said model.

15. The method of claim 9, wherein said three-dimensional model of teeth comprises a model of a proposed arrangement of teeth in the upper and lower arches for planning orthodontic treatment of said patient.

16. The method of claim 9, wherein said three-dimensional model of teeth comprises a model of an initial malocclusion of the patent.

17. The method of claim 9, wherein said three-dimensional model of teeth comprises a model of an intermediate position of teeth during the course of treatment of said patient.

* * * * *